(12) United States Patent
Kristen et al.

(10) Patent No.: US 6,933,400 B2
(45) Date of Patent: Aug. 23, 2005

(54) COMPLEX COMPOUNDS AND THEIR USE IN OLEFIN POLYMERIZATION

(75) Inventors: Marc Oliver Kristen, Limburgerhof (DE); Benno Bildstein, Innsbruck (AT); Alexander Krajete, Salzburg (AT)

(73) Assignee: BASF Aktiengesellschaft, Ludwigshafen (DE)

( * ) Notice: Subject to any disclaimer, the term of this patent is extended or adjusted under 35 U.S.C. 154(b) by 33 days.

(21) Appl. No.: 10/467,931

(22) PCT Filed: Feb. 7, 2002

(86) PCT No.: PCT/EP02/01264

§ 371 (c)(1),
(2), (4) Date: Aug. 13, 2003

(87) PCT Pub. No.: WO02/064645

PCT Pub. Date: Aug. 22, 2002

(65) Prior Publication Data

US 2004/0054208 A1 Mar. 18, 2004

(30) Foreign Application Priority Data

Feb. 13, 2001 (DE) .......................... 101 06 902

(51) Int. Cl.$^7$ .......................... C07F 15/04; C07F 7/00; B01J 31/00; C08F 4/44
(52) U.S. Cl. .......................... 556/137; 556/39; 556/45; 556/46; 556/57; 556/58; 556/138; 526/161; 526/172; 502/103; 502/117; 502/152; 502/156
(58) Field of Search .............................. 556/39, 45, 46, 556/57, 58, 137, 138; 526/161, 172; 502/103, 117, 152, 156

(56) References Cited

FOREIGN PATENT DOCUMENTS

| DE | 199 61 340 | 7/2001 |
|---|---|---|
| EP | 0 874 005 | 10/1998 |
| WO | 96/23010 | 8/1996 |
| WO | 98/27124 | 6/1998 |
| WO | 98 30609 | 7/1998 |
| WO | 98/24554 | 10/1998 |
| WO | 98/42664 | 10/1998 |
| WO | 98 42664 | 10/1998 |
| WO | 98 42665 | 10/1998 |
| WO | 01 44325 | 6/2001 |

OTHER PUBLICATIONS

C.L. Honeybourne et al.: "Spectroscopic study of two hydrazine derivatives and some of their metal complexes" Database CA 'Online!Chemical Abstracts Service, Database accession No. 74:69593, XP002209587.

H.H. Brintzinger et al. Angew. Chem., vol. 107, pp. 1255–1283, 1995.

A. Tomov et al. Macromol. Symp., vol. 150, pp. 53–58, 2000.

Primary Examiner—Porfirio Nazario-Gonzalez
(74) Attorney, Agent, or Firm—Oblon, Spivak, McClelland, Maier & Neustadt, P.C.

(57) ABSTRACT

Complexes of the formulae I a to d,

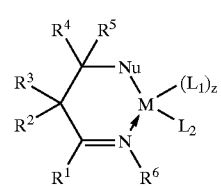

I a

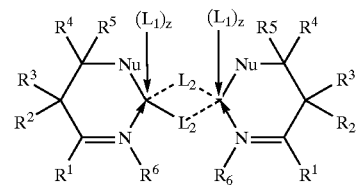

I b

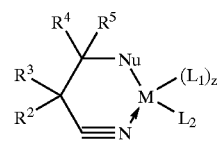

I c

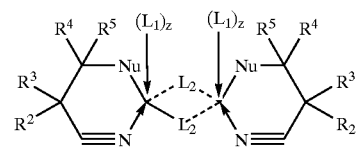

I d where M is an element of groups 6 to 10 of the Periodic Table of the Elements, preferably Ni, can be used for the polymerization and copolymerization of olefins, for example in suspension polymerization processes, gas-phase polymerization processes, bulk polymerization processes and emulsion polymerization processes.

9 Claims, No Drawings

COMPLEX COMPOUNDS AND THEIR USE IN OLEFIN POLYMERIZATION

The present invention relates to complexes of the formulae I a to d,

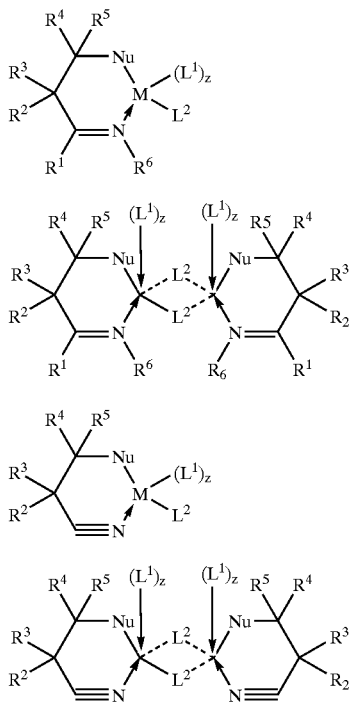

where the variables are defined as follows:
M is an element of groups 6 to 10 of the Periodic Table of the Elements in the oxidation state +2 to +4,
Nu is selected from among O, S and N—$R^7$;
$R^1$ to $R^7$ are selected from among hydrogen,
  $C_1$–$C_8$-alkyl, substituted or unsubstituted,
  $C_2$–$C_8$-alkenyl, substituted or unsubstituted, having from one to 4 isolated or conjugated double bonds;
  $C_3$–$C_{12}$-cycloalkyl, substituted or unsubstituted, $C_7$–$C_{13}$-aralkyl,
  $C_6$–$C_{14}$-aryl, unsubstituted or substituted by one or more identical or different substituents selected from among
    $C_1$–$C_8$-alkyl, substituted or unsubstituted,
    $C_3$–$C_{12}$-cycloalkyl,
    $C_7$–$C_{13}$-aralkyl,
    $C_6$–$C_{14}$-aryl,
    halogen,
    $C_1$–$C_6$-alkoxy, substituted or unsubstituted,
    $C_6$–$C_{14}$-aryloxy,
    $SiR^8R^9R^{10}$ and O—$SiR^8R^9R^{10}$;
  five- and six-membered nitrogen-containing heteroaryl radicals, unsubstituted or substituted by one or more identical or different substituents selected from among
    $C_1$–$C_8$-alkyl, substituted or unsubstituted,
    $C_3$–$C_{12}$-cycloalkyl,
    $C_7$–$C_{13}$-aralkyl,
    $C_6$–$C_{14}$-aryl,
    halogen,
    $C_1$–$C_6$-alkoxy,
    $C_6$–$C_{14}$-aryloxy,
    $SiR^8R^9R^{10}$ and O—$SiR^8R^9R^{10}$;
where adjacent radicals $R^1$ to $R^7$ may be joined to one another to form a 5- to 12-membered ring;
$L^1$ is an uncharged, organic or inorganic ligand,
$L^2$ is an organic or inorganic anionic ligand, where $L^1$ and $L^2$ may be joined to one another by one or more covalent bonds,
z is an integer from 1 to 3,
$R^8$ to $R^{10}$ are identical or different and are selected from among hydrogen, $C_1$–$C_8$-alkyl, $C_3$–$C_{12}$-cycloalkyl, $C_7$–$C_{13}$-aralkyl and $C_6$–$C_{14}$-aryl.

The present invention also relates to a process for preparing the novel complexes from ligands of the formula II, and a process for the polymerization or copolymerization of olefins using a complex of the formula I.

Furthermore, the present invention relates to a process for preparing supported polymerization catalysts using the novel complex of the formula I, and to a process for the polymerization or copolymerization of olefins using the novel supported catalysts.

Finally, the present invention relates to a process for the emulsion polymerization and copolymerization of olefins using a complex having one of the formulae I a to I d.

Polymers and copolymers of olefins are of great economic importance because the monomers are readily available in large quantities and because the polymers can be varied within a wide range by variation of the method of preparation or the processing parameters. The catalyst used is of particular significance in the process for preparing the polymers. Apart from Ziegler-Natta catalysts, various single-site catalysts are of increasing importance. In the latter, central atoms which have been examined in some detail include not only Zr as in, for example, metallocene catalysts (H.-H. Brintzinger et al., Angew. Chem. 1995, 107, 1255) but also Ni or Pd (WO 96/23010) or Fe and Co (e.g. WO 98/27124). The complexes of Ni, Pd, Fe and Co are also referred to as complexes of late transition metals.

Metallocene catalysts have disadvantages for industrial use. The most frequently employed metallocenes, namely zirconocenes and hafnocenes, are sensitive to hydrolysis. In addition, most metallocenes are sensitive to many catalyst poisons such as alcohols, ethers and CO, which makes it necessary for the monomers to be carefully purified.

While Ni and Pd complexes (WO 96/23010) catalyze the formation of highly branched polymers which are of little commercial interest, the use of Fe or Co complexes leads to formation of highly linear polyethylene containing very low proportions of comonomer.

Furthermore, complexes by means of which ethylene can be polymerized or copolymerized in the presence of water have been studied.

WO 98/42664 describes complexes of the formula A and closely related derivatives containing salicylaldimine ligands and also their use for the polymerization of olefins.

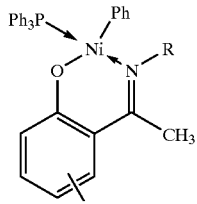

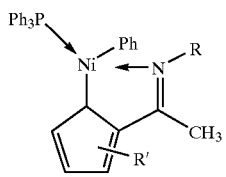

WO 98/42665 describes complexes of the formula B and closely related derivatives and also their use for the polymerization of olefins. In the complexes of both the formula A and the formula B, the radical R on the imine nitrogen is a $C_1$–$C_{11}$-alkyl group or an ortho-substituted phenyl group. However, their activity should be capable of improvement.

It is also known that the complexes of the formulae A and B are polymerization-active even in the presence of small amounts of water, without the catalytic activity being adversely affected (WO 98/42664, in particular page 17, line 14 ff; WO 98/42665, p. 16, line 13). However, these amounts of water must not exceed 100 equivalents, based on the complex (WO 98/42664, page 17, lines 33–35; WO 98/42665, page 16, lines 30–31). However, an emulsion polymerization cannot be carried out under these conditions. In Macromol. Symp. 2000, 150, 53, A. Tomov et al. reported that some binuclear Ni complexes are suitable as catalysts for emulsion polymerization of ethylene. However, the synthesis of the complexes mentioned is complicated.

WO 98/30609 discloses derivatives of A which are suitable for the polymerization of ethylene and propylene. However, their activity is not always satisfactory.

EP-A 0 874 005 discloses further polymerization-active complexes. These are preferably Ti complexes with salicylaldimine ligands. These too bear phenyl substituents or substituted phenyl substituents on the aldimine nitrogen (pages 18–23) or else the aldimine nitrogen is incorporated into a 6-membered ring (pages 31–32). However, they are very sensitive to polar compounds such as water, alcohols or ethers.

In DE-A 199 61 340 it is shown that complexes of late transition metals having the formulae C and D

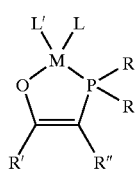

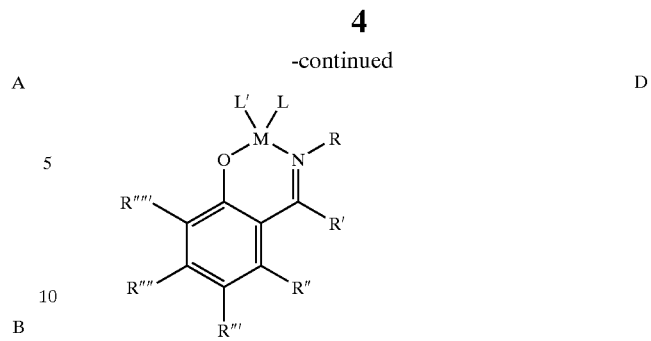

where R to R'''' are each hydrogen, alkyl, $C_7$–$C_{13}$-aralkyl or $C_6$–$C_{14}$-aryl, and mixtures thereof are suitable for polymerizing ethylene by emulsion polymerization. However, the activities should be capable of improvement. In A. Held et al., J. Chem. Soc., Chem. Commun. 2000, 301, it is shown that complexes of the formula C in which R is phenyl and R'' is an $SO_3$—group will polymerize ethylene in an aqueous medium. The activity of C, too, is not yet optimal.

Owing to the great commercial importance of polyolefins, the search for very versatile polymerization-active complexes having the highest possible activity continues to be of great importance.

It is an object of the present invention,
- to provide new complexes which are suitable for the polymerization of olefins;
- to provide a process for preparing the complexes of the present invention;
- to provide a process for the polymerization or copolymerization of olefins using the complexes of the present invention;
- to provide supported catalysts for the polymerization of olefins and a process for preparing the supported catalysts of the present invention using the complexes of the present invention;
- to polymerize and copolymerize olefins using the supported catalysts of the present invention;
- to provide a process for the emulsion polymerization or copolymerization of olefins, in particular ethylene, using the complexes of the present invention.

We have found that this object is achieved by means of complexes having the structures of the formulae I a to d defined at the outset.

In the formulae I a to d, the variables are defined as follows: M is an element of groups 6 to 10 of the Periodic Table of the Elements in the oxidation state from +2 to +4; preferably Cr, Fe, Pd or Ni, particularly preferably Ni.

Nu is selected from among O, S and N—$R^7$, with oxygen being preferred;

$R^1$ to $R^7$ are identical or different and are selected from among hydrogen, $C_1$–$C_{18}$-alkyl groups, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl n-octyl, n-decyl, n-dodecyl and n-octadecyl; preferably $C_1$–$C_{12}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl and n-decyl, particularly preferably $C_1$–$C_4$-alkyl such as methyl, ethyl, n-propyl, isopropyl, n-butyl, isobutyl, sec-butyl and tert-butyl;

examples of substituted $C_1$–$C_{18}$-alkyl groups are: monohalogenated or polyhalogenated $C_1$–$C_8$-alkyl groups such as fluoromethyl, difluoromethyl, trifluoromethyl, chloromethyl, dichloromethyl, trichloromethyl, bromomethyl, dibromomethyl, tribromomethyl, pentafluoroethyl, perfluoropropyl and perfluorobutyl, particularly preferably fluoromethyl, difluoromethyl, trifluoromethyl and perfluorobutyl;

$C_2$–$C_{18}$-alkenyl having from one to 4 isolated or conjugated double bonds, for example vinyl, 1-allyl, 3-allyl, ω-butenyl, ω-pentenyl, ω-hexenyl, 1-cis-buta-1,3-dienyl and 1-cis-hexa-1,5-dienyl.

examples of substituted $C_2$–$C_{18}$-alkenyl groups are: isopropenyl, 1-isoprenyl, α-styryl, β-styryl, 1-cis-1,2-phenylethenyl and 1-trans-1,2-phenylethenyl.

$C_3$–$C_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preferably cyclopentyl, cyclohexyl and cycloheptyl;

examples of substituted cycloalkyl groups are: 2-methylcyclopentyl, 3-methylcyclopentyl, cis-2,4-dimethylcyclopentyl, trans-2,4-dimethylcyclopentyl, cis-2,5-dimethylcyclopentyl, trans-2,5-dimethylcyclopentyl, 2,2,5,5-tetramethylcyclopentyl, 2-methylcyclohexyl, 3-methylcyclohexyl, 4-methylcyclohexyl, cis-2,6-dimethylcyclohexyl, trans-2,6-dimethylcyclohexyl, cis-2,6-diisopropylcyclohexyl, trans-2,6-diisopropylcyclohexyl, 2,2,6,6-tetramethylcyclohexyl, 2-methoxycyclopentyl, 2-methoxycyclohexyl, 3-methoxycyclopentyl, 3-methoxycyclohexyl, 2-chlorocyclopentyl, 3-chlorocyclopentyl, 2,4-dichlorocyclopentyl, 2,2,4,4-tetrachlorocyclopentyl, 2-chlorocyclohexyl, 3-chlorocyclohexyl, 4-chlorocyclohexyl, 2,5-dichlorocyclohexyl, 2,2,6,6-tetrachlorocyclohexyl, 2-thiomethylcyclopentyl, 2-thiomethylcyclohexyl, 3-thiomethylcyclopentyl, 3-thiomethylcyclohexyl and further derivatives;

$C_7$–$C_{13}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl;

$C_6$–$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl;

$C_6$–$C_{14}$-aryl such as phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl substituted by one or more identical or different substituents selected from among $C_1$–$C_{18}$-alkyl groups such as methyl, ethyl, n-propyl, isopropyl, h-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl n-octyl, n-decyl, n-dodecyl and n-octadecyl, preferably $C_1$–$C_{12}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl and n-decyl, particularly preferably $C_1$–$C_4$-alkyl such as methyl, ethyl, n-propyl, isopropyl, n-butyl, isobutyl, sec-butyl and tert-butyl;

examples of substituted $C_1$–$C_{18}$-alkyl groups are: monohalogenated or polyhalogenated $C_1$–$C_8$-alkyl groups such as fluoromethyl, difluoromethyl, trifluoromethyl, chloromethyl, dichloromethyl, trichloromethyl, bromomethyl, dibromomethyl, tribromomethyl, pentafluoroethyl, perfluoropropyl and perfluorobutyl, particularly preferably fluoromethyl, difluoromethyl, trifluoromethyl and perfluorobutyl;

$C_2$–$C_{18}$-alkenyl having from one to 4 isolated or conjugated double bonds, for example vinyl, 1-allyl, 3-allyl, ω-butenyl, ω-pentenyl, ω-hexenyl, 1-cis-buta-1,3-dienyl and 1-cis-hexa-1,5-dienyl.

examples of substituted $C_2$–C8-alkenyl groups are: isopropenyl, 1-isoprenyl, α-styryl, β-styryl, 1-cis-1,2-phenylethenyl and 1-trans-1,2-phenylethenyl.

$C_3$–$C_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preferably cyclopentyl, cyclohexyl and cycloheptyl;

$C_7$–$C_{13}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl;

$C_6$–$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl;

halogen, for example fluorine, chlorine, bromine and iodine, particularly preferably fluorine and chlorine;

$C_1$–$C_6$-alkoxy groups such as methoxy, ethoxy, n-propoxy, isopropoxy, n-butoxy, isobutoxy, sec-butoxy, tert-butoxy, n-pentoxy, isopentoxy, n-hexoxy and isohexoxy, particularly preferably methoxy, ethoxy, n-propoxy and n-butoxy;

$C_6$–$C_{14}$-aryloxy groups such as phenoxy, ortho-cresyloxy, meta-cresyloxy, para-cresyloxy, α-naphthoxy, β-naphthoxy and 9-anthryloxy;

silyl groups $SiR^8R^9R^{10}$, where $R^8$ to $R^{10}$ are selected independently from among hydrogen, $C_1$–$C_8$-alkyl groups, benzyl radicals and $C_6$–$C_{14}$-aryl groups; with preference being given to the trimethylsilyl, triethylsilyl, triisopropylsilyl, diethylisopropylsilyl, dimethylhexylsilyl, tert-butyldimethylsilyl, tert-butyldiphenylsilyl, tribenzylsilyl, triphenylsilyl and tri-para-xylylsilyl groups and particular preference being given to the trimethylsilyl group and the tert-butyldimethylsilyl group;

silyloxy groups $OSiR^8R^9R^{10}$, where $R^8$ to $R^{10}$ are selected independently from among hydrogen, $C_1$–$C_8$-alkyl groups, benzyl radicals and $C_6$–$C_{14}$-aryl groups; with preference being given to the trimethylsilyloxy, triethylsilyloxy, triisopropylsilyloxy, diethylisopropylsilyloxy, dimethylthexylsilyloxy, tert-butyldimethylsilyloxy, tert-butyldiphenylsilyloxy, tribenzylsilyloxy, triphenylsilyloxy and tri-para-xylylsilyloxy groups and particular preference being given to the trimethylsilyloxy group and the tert-butyldimethylsilyloxy group;

five and six-membered nitrogen-containing heteroaryl radicals such as N-pyrrolyl, pyrrol-2-yl, pyrrol-3-yl, N-imidazolyl, 2-imidazolyl, 4-imidazolyl, 1,2,4-triazol-3-yl, 1,2,4-triazol-4-yl, 2-pyridyl, 3-pyridyl, 4-pyridyl, 3-pyridazinyl, 4-pyridazinyl, 2-pyrimidinyl, 4-pyrimidinyl, 5-pyrimidinyl, N-indolyl and N-carbazolyl;

five- and six-membered nitrogen-containing heteroaryl radicals such as N-pyrrolyl, pyrrol-2-yl, pyrrol-3-yl, N-imidazolyl, 2-imidazolyl, 4-imidazolyl, 1,2,4-triazol-3-yl, 1,2,4-triazol-4-yl, 2-pyridyl, 3-pyridyl, 4-pyridyl, 3-pyridazinyl, 4-pyridazinyl, 2-pyrimidinyl, 4-pyrimidinyl, 5-pyrimidinyl, N-indolyl and N-carbazolyl substituted by one or more identical or different substituents selected from among $C_1$–$C_{18}$-alkyl groups such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl n-octyl, n-decyl, n-dodecyl and n-octadecyl, preferably $C_1$–$C_{12}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl and n-decyl, particularly preferably $C_1$–$C_4$-alkyl such as methyl, ethyl, n-propyl, isopropyl, n-butyl, isobutyl, sec-butyl and tert-butyl;

examples of substituted $C_1$–$C_{18}$-alkyl groups are: monohalogenated or polyhalogenated $C_1$–$C_8$-alkyl groups such as fluoromethyl, difluoromethyl, trifluoromethyl, chloromethyl, dichloromethyl, trichloromethyl, bromomethyl, dibromomethyl, tribromomethyl, pentafluoroethyl, perfluoropropyl and perfluorobutyl, particularly preferably fluoromethyl, difluoromethyl, trifluoromethyl and perfluorobutyl;

$C_2$–$C_{18}$-alkenyl having from one to 4 isolated or conjugated double bonds, for example vinyl, 1-allyl, 3-allyl, ω-butenyl, ω-pentenyl, ω-hexenyl, 1-cis-buta-1,3-dienyl and 1-cis-hexa-1,5-dienyl.

examples of substituted $C_2$–$C_8$-alkenyl groups are: isopropenyl, 1-isoprenyl, α-styryl, β-styryl, 1-cis-1,2-phenylethenyl and 1-trans-1,2-phenylethenyl.

$C_3$–$C_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preferably cyclopentyl, cyclohexyl and cycloheptyl;

$C_7$–$C_{13}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl;

$C_6$–$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl;

halogen, for example fluorine, chlorine, bromine and iodine, particularly preferably fluorine and chlorine;

$C_1$–$C_6$-alkoxy groups such as methoxy, ethoxy, n-propoxy, isopropoxy, n-butoxy, isobutoxy, sec-butoxy, tert-butoxy, n-pentoxy, isopentoxy, n-hexoxy and isohexoxy, particularly preferably methoxy, ethoxy, n-propoxy and n-butoxy;

$C_6$–$C_{14}$-aryloxy groups such as phenoxy, ortho-cresyloxy, meta-cresyloxy, para-cresyloxy, α-naphthoxy, β-naphthoxy and 9-anthryloxy;

silyl groups $SiR^8R^9R^{10}$, where $R^8$ to $R^{10}$ are selected independently from among hydrogen, $C_1$–$C_8$-alkyl groups, benzyl radicals and $C_6$–$C_{14}$-aryl groups; with preference being given to the trimethylsilyl, triethylsilyl, triisopropylsilyl, diethylisopropylsilyl, dimethylhexylsilyl, tert-butyldimethylsilyl, tert-butyldiphenylsilyl, tribenzylsilyl, triphenylsilyl and tri-para-xylylsilyl groups and particular preference being given to the trimethylsilyl group and the tert-butyldimethylsilyl group;

silyloxy groups $OSiR^8R^9R^{10}$, where $R^8$ to $R^{10}$ are selected independently from among hydrogen, $C_1$–$C_8$-alkyl groups, benzyl radicals and $C_6$–$C_{14}$-aryl groups; with preference being given to the trimethylsilyloxy, triethylsilyloxy, triisopropylsilyloxy, diethylisopropylsilyloxy, dimethylthexylsilyloxy, tert-butyldimethylsilyloxy, tert-butyldiphenylsilyloxy, tribenzylsilyloxy, triphenylsilyloxy and tri-para-xylylsilyloxy groups and particular preference being given to the trimethylsilyloxy group and the tert-butyldimethylsilyloxy group.

In a particular embodiment, adjacent radicals $R^1$ to $R^7$ may be joined to one another to form a 5- to 12-membered ring. For example, $R^1$ and $R^6$ may together be: —$(CH_2)_3$— (trimethylene), —$(CH_2)_4$—(tetramethylene), —$(CH_2)_5$— (pentamethylene), —$(CH_2)_6$—(hexamethylene), —$CH_2$—CH=CH—, —$CH_2$—CH=CH—$CH_2$—, —CH=CH—CH=CH—, —O—$CH_2$—O—, —O—CHMe—O—, —O—CH—$(C_6H_5)$—O—, —O—$CH_2$—$CH_2$—O—, —NMe—$CH_2$—$CH_2$—NMe—, —NMe—$CH_2$—NMe— or —O—$SiMe_2$—O— where Me=$CH_3$. In a preferred example, $R^1$ and $R^6$ together form a 1,3-butadiene-1,4-diyl unit which may in turn be monosubstituted or polysubstituted by $C_1$–$C_8$-alkyl. In a further preferred example $R^2$ and $R^4$ together form a 1,3-butadien-1,4-diyl unit which may in turn be monosubstituted or polysubstituted by $C_1$–$C_8$-alkyl.

$L^1$ is selected from among uncharged, inorganic and organic ligands, for example phosphines of the formula $(R^{11})_x PH_{3-x}$ or amines of the formula $(R^{11})_x NH_{3-x}$, where x is an integer from 0 to 3. However, ethers $(R^{11})_2O$ such as dialkyl ethers, e.g. diethyl ethers, or cyclic ethers, e.g. tetrahydrofuran, $H_2O$, alcohols $(R^{11})OH$ such as methanol or ethanol, pyridine, pyridine derivatives of the formula $C_5H_{5-x}(R^{13})_xN$, for example 2-picoline, 3-picoline, 4-picoline, 2,3-lutidine, 2,4-lutidine, 2,5-lutidine, 2,6-lutidine or 3,5-lutidine, CO, $C_1$–$C_{12}$-alkylnitriles or $C_6$–$C_{14}$-arylnitriles, e.g. acetonitrile, propionitrile, butyronitrile or benzonitrile, are also suitable. It is also possible to use singly or multiply ethylenically unsaturated double bond systems such as ethenyl, propenyl, cis-2-butenyl, trans-2-butenyl, cyclohexenyl or norbornenyl as ligand.

$L^2$ is selected from among inorganic and organic anionic ligands, for example from among halide ions such as fluoride, chloride, bromide and iodide, preferably chloride and bromide, amide anions $(R^{11})_{x-1}NH_{2-x}$, where x is an integer from 0 to 3, $C_1$–$C_6$-alkyl anions such as $(CH_3)$—, $(C_2H_5)$—, $(C_3H_7)$—, (n-$C_4H_9$)—, (tert-$C_4H_9$)— and $(C_6H_{14})$—;

allyl anions and methallyl anions, benzyl anions and aryl anions such as $(C_6H_5)$—.

z is an integer from 1 to 3, e.g. 0, 1, 2 or 3;

$R^1$ are identical or different and are selected from among
hydrogen,
$C_1$–$C_8$-alkyl groups,
benzyl radicals and
$C_6$–$C_{14}$-aryl groups, where these groups are as defined above and where 2 radicals $R^{11}$ may be covalently bound to one another.

In a particular embodiment, $L^1$ and $L^2$ are joined to one another by one or more covalent bonds. Examples for such ligands are 1,5-cyclooctadienyl ligands ("COD"), 1,6-cyclodecenyl ligands and 1,5,9-all-trans-cyclododecatrienyl ligands.

In a further particular embodiment, $L^1$ is tetramethylethylenediamine, with only one nitrogen coordinating to the nickel.

The novel complexes of the formulae I a to d are generally prepared from ligands of the formula II a or II b, in which the variables are as defined above. To synthesize the complexes of the present invention, the ligands are firstly deprotonated by means of a base and subsequently reacted with metal compounds of the formula $MX_2$, $MX_3$, $MX_4$ or $ML^1L^2$.

Bases which can be used are the metal alkyls customary in organometallic chemistry, for example methyllithium, ethyllithium, n-butyllithium, sec-butyllithium, tert-butyllithium or hexyllithium, also Grignard compounds such as ethylmagnesium bromide, also lithium amide, sodium amide, potassium amide, potassium hydride or lithium diisopropylamide ("LDA"). Solvents which have been found to be useful are high-boiling solvents such as toluene, ortho-xylene, meta-xylene, para-xylene, ethylbenzene or mixtures of these, also acyclic or cyclic ethers such as 1,2-dimethoxyethane, tetrahydrofuran or diethyl ether.

This deprotonation is generally complete after a few hours; it is appropriate to employ a reaction time of from 2 to 10 hours, preferably from 3 to 5 hours. The temperature conditions are generally not critical; temperatures of from –90° C. to –20° C. are preferred for the deprotonation.

The deprotonated ligand and the metal compound of the formula $MX_2$, $MX_3$, $MX_4$ or $ML^1L^2$ are subsequently reacted with one another.

X are identical or different and are selected from among:
halogen such as fluorine, chlorine, bromine and iodine, preferably chlorine and bromine;
$C_1$–$C_8$-alkyl groups such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl and n-octyl; preferably $C_1$–$C_6$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, particularly preferably $C_1$–$C_4$-alkyl such as methyl, ethyl, n-propyl, isopropyl, n-butyl, isobutyl, sec-butyl and tert-butyl;
$C_3$–$C_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preferably cyclopentyl, cyclohexyl and cycloheptyl;
$C_7$–$C_{13}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl;
$C_6$–$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl;

X are preferably identical.

$MX_2$, $MX_3$, $MX_4$ or $ML^1L^2$ can optionally be stabilized by uncharged ligands. Possible uncharged ligands are the customary ligands of coordination chemistry, for example cyclic and acyclic ethers, amines, diamines, nitriles, isonitriles or phosphines. Particular preference is given to diethyl ether, tetrahydrofuran, 1,2-dimethoxyethane, tetramethylethylenediamine, acetonitrile or triphenylphosphine. Particularly in cases in which, for example, Ni-dialkyl compounds are to be used, uncharged ligands have been found to be useful. The uncharged ligands can also be used as solvents.

The conditions for the reaction are not critical per se; it is usual to mix the deprotonated ligand II and $MX_2$, $MX_3$, $MX_4$ and $ML^1L^2$ with one another in a suitable solvent such as benzene, toluene, ethylbenzene, ortho-xylene, meta-xylene or para-xylene, chlorobenzene, cyclohexane, acetonitrile, tetrahydrofuran, methylene chloride or a mixture of these. The temperature can be in the range from –100° C. to +150° C., preferably from –78° C. to +100° C. It is important that the reaction is carried out in the absence of oxygen and moisture.

The molar ratio of ligand to M can be in the range from 5:1 to 1:5. However, since the ligands of the formula II are more difficult to obtain than the metal compounds, molar ratios of ligand:M in the range from 1:1 to 1:3 are preferred. Particular preference is given to stoichiometric amounts.

The novel complexes of the formulae I a to d can be purified by the methods customary in organometallic chemistry, with particular preference being given to crystallization. Filtration via filter aids such as Celite® is also useful.

For the polymerization, it is not necessary in all cases to isolate the complexes of the present invention. It is also possible to react a ligand of the formula II with a suitable metal compound of the formula $MX_2$, $MX_3$, $MX_4$ or $ML^1L^2$ only immediately prior to the polymerization and generate the complex in situ.

If X in the metal compound of the formula $MX_2$, $MX_3$ or $MX_4$ is selected from the group consisting of $C_1$–$C_8$-alkyl groups, $C_3$–$C_{12}$-cycloalkyl groups, $C_7$–$C_{13}$-aralkyl groups and $C_6$–$C_{14}$-aryl groups, the deprotonation of the ligand of the formula II can be omitted. In these cases, it has been found to be preferable not to isolate the complexes of the present invention but instead to generate them in situ only immediately prior to the polymerization.

The preparation of the ligands of the formula II a and II b is described in the parallel patent applications DE-A 10107045 and DE-A 10107043. They can be obtained by reacting a deprotonated imine or nitrile having an acidic a-H atom with an electrophilic compound of the formula III

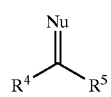

III where the variables are as defined above.

It has been found that the novel complexes of the formulae I a to I d are suitable for polymerizing olefins. They are particularly useful for polymerizing and copolymerizing ethylene and propylene to form high molecular weight polymers.

For the novel complexes of the formulae I a to d to be catalytically active, they have to be activated. Suitable activators are selected aluminum and boron compounds bearing electron-withdrawing radicals (e.g. trispentafluorophenylborane, trispentafluorophenylaluminum, N,N-dimethylanilinium tetrakispentafluorophenylborate, tri-n-butylammonium tetrakispentafluorophenylborate, N,N-dimethylanilinium tetrakis(3,5-bisperfluoromethyl)phenylborate, tri-n-butylammonium tetrakis(3,5-bisperfluoromethyl) phenylborate and tritylium tetrakispentafluorophenylborate). Preference is given to dimethylanilinium tetrakispentafluorophenylborate, tritylium tetrakispentafluorophenylborate and trispentafluorophenylboran.

If boron or aluminum compounds are used as activators for the novel complexes of the formulae I a to d, they are generally used in a molar ratio of from 1:10 to 10:1, based on M; they are preferably used in a ratio of from 1:2 to 5:1 and particularly preferably in stoichiometric amounts.

Another suitable class of activators are aluminoxanes.

The structure of the aluminoxanes is not known precisely. They are products which are obtained by careful partial hydrolysis of aluminum alkyls (cf. DE-A 30 07 725). These products are not in the form of pure chemical compounds, but are mixtures of open-chain and cyclic structures of the types IV a and IV b. These mixtures are presumably in dynamic equilibrium.

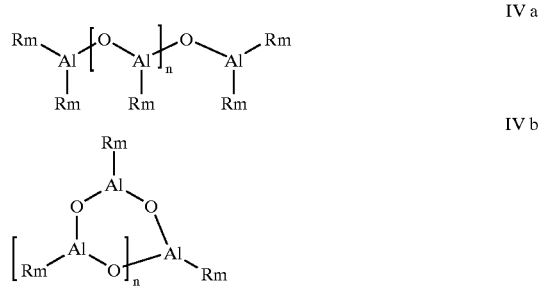

IV a

IV b

In the formulae IV a and IV b the radicals $R^m$ are each $C_1$–$C_{12}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl, n-octyl, n-nonyl, n-decyl or n-dodecyl, preferably $C_1$–$C_6$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, particularly preferably methyl;

$C_3$–$C_{12}$-cycloalkyl such as cyclopropyl, cyclobutyl, cyclopentyl, cyclohexyl, cycloheptyl, cyclooctyl, cyclononyl, cyclodecyl, cycloundecyl or cyclododecyl, preferably cyclopentyl, cyclohexyl or cycloheptyl;

$C_7$–$C_{20}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, 1-phenylbutyl, 2-phenylbutyl, 3-phenylbutyl or 4-phenylbutyl, particularly preferably benzyl, or $C_6$–$C_{14}$-aryl such as phenyl, 1-naphthyl, 2-naphthyl, 1-anthryl, 2-anthryl, 9-anthryl, 1-phenanthryl, 2-phenanthryl, 3-phenanthryl, 4-phenanthryl or 9-phenanthryl, preferably phenyl, 1-naphthyl or 2-naphthyl, particularly preferably phenyl; and n is an integer from 0 to 40, preferably from 1 to 25 and particularly preferably from 2 to 22.

Cage-like structures for aluminoxanes are also discussed in the literature (Y. Koide, S. G. Bott, A. R. Barron Organometallics 1996, 15, 2213–26; A. R. Barron Macromol. Symp. 1995, 97, 15–25). Regardless of the actual structure of the aluminoxanes, they are suitable as activators for the novel metal complexes of the formula I.

Mixtures of various aluminoxanes are particularly preferred activators in cases when the polymerization is carried out in a solution in a paraffin, for example n-heptane or isododecane. A particularly preferred mixture is the CoMAO available commercially from Witco GmbH, which has the formula $[(CH_3)_{0.9}(iso-C_4H_9)_{0.1}AlO]_n$.

To activate the complexes of the formulae I a to d by means of aluminoxanes, an excess of aluminoxane, based on M, is generally necessary. Appropriate molar ratios of M:Al are in the range from 1:10 to 1:10 000, preferably from 1:50 to 1:1000 and particularly preferably from 1:100 to 1:500.

It is generally believed that activators for metal complexes of the formulae I a to d abstract a ligand $L^1$ or $L^2$. Instead of aluminum alkyl compounds of the formula III a or III b or the above-described aluminum or boron compounds having electron-withdrawing radicals, the activator can also be, for example, an olefin complex of rhodium or nickel.

Preferred nickel-(olefin)$_y$-complexes, where y=1, 2, 3 or 4, available commercially from Aldrich are $Ni(C_2H_4)_3$, $Ni(1,5$-cyclooctadiene$)_2$ "$Ni(COD)_2$", $Ni(1,6$-cyclodecadiene$)_2$ or $Ni(1,5,9$-all-trans-cyclododecatriene$)_2$. Particular preference is given to $Ni(COD)_2$.

Particularly useful activators of this type are mixed ethylene/1,3-dicarbonyl complexes of rhodium, for example ethylenerhodium acetylacetonate $Rh(acac)(CH_2=CH_2)_2$, ethylenerhodium benzoylacetonate $Rh(C_6H_5—CO—CH—CO—CH_3)(CH_2=CH_2)_2$ or $Rh(C_6H_5—CO—CH—CO—C_6H_5)(CH_2=CH_2)_2$. $Rh(acac)(CH_2=CH_2)_2$ is suitable. This compound can be synthesized by the method of R. Cramer in Inorg. Synth. 1974, 15, 14.

Some of the complexes of the formula I can be activated by ethylene. The ease of the activation reaction depends critically on the nature of the ligand $L^1$.

Depending on the synthesis conditions, the complexes of the present invention can be obtained as monomers or else as dimers which are bridged via two of the substituents $L^2$. The activation does not depend critically on whether the complexes are in monomeric or dimeric form.

The chosen complex of the formula I and the activator together form a catalyst system.

The activity of the catalyst system of the invention can be increased by addition of further aluminum alkyl of the formula $Al(R^m)_3$ or aluminoxanes, particularly when compounds of the formula IV a or IV b or the abovementioned aluminum or boron compounds having electron-withdrawing radicals are used as activators; aluminum alkyls of the formula $Al(R^m)_3$ or aluminoxanes can also act as molar mass regulators. A further effective molar mass regulator is hydrogen. The molar mass can be regulated particularly effectively via the reaction temperature and the pressure. If a boron compound as described above is to be used, the addition of an aluminum alkyl of the formula $Al(R^m)_3$ is particularly preferred.

It has been found that the novel complexes of the formulae I a to d are suitable for polymerizing olefins. They are particularly useful for polymerizing and copolymerizing ethylene and propylene.

Pressure and temperature conditions during the polymerization can be chosen within wide limits. Pressures in a range from 0.5 bar to 4000 bar have been found to be useful; preference is given to from 10 to 75 bar or high-pressure conditions of from 500 to 2500 bar. A suitable temperature range has been found to be from 0 to 120° C., preferably from 40 to 100° C. and particularly preferably from 50 to 85° C.

As monomers, mention may be made of the following olefins: ethylene, propylene, 1-butene, 1-pentene, 1-hexene, 1-octene, 1-decene and 1-undecene, with propylene and ethylene being preferred and ethylene being particularly preferred.

Suitable comonomers are a-olefins, for example from 0.1 to 20 mol % of 1-butene, 1-pentene, 1-hexene, 4-methyl-1-pentene, 1-octene, 1-decene or 1-undecene. Further suitable comonomers are isobutene and styrene, also internal olefins such as cyclopentene, cyclohexene, norbornene and norbornadiene.

Solvents which have been found to be suitable are toluene, ortho-xylene, meta-xylene, para-xylene and ethylbenzene and also mixtures of these, such as diethyl ether, tetrahydrofuran, chlorobenzene, 1,3-dichlorobenzene, dichloromethane and also, under high-pressure conditions, supercritical ethylene.

Hydrogen has been found to be an effective chain transfer agent in polymerizations using the novel complexes of the formula I, i.e. the molecular weight of the polymers obtainable by means of the catalyst system of the present invention can be reduced by addition of hydrogen. If sufficient hydrogen is added, waxes are obtained. The hydrogen concentration required for this depends, inter alia, on the type of polymerization plant employed.

For the catalyst systems of the present invention to be able to be used in modern polymerization processes such as suspension processes, bulk polymerization processes or gas-phase processes, they have to be immobilized on a solid support. Otherwise, morphology problems with the polymer (lumps, deposits on walls, blockages in lines or heat exchangers) can occur and force shutdown of the plant. Such an immobilized catalyst system will be referred to as a catalyst.

It has been found that the catalyst systems of the present invention can be readily deposited on solid support materials. Suitable support materials are, for example, porous metal oxides of metals of groups 2 to 14 or mixtures thereof, also sheet silicates and zeolites. Preferred examples of metal oxides of groups 2 to 14 are $SiO_2$, $B_2O_3$, $Al_2O_3$, MgO, CaO and ZnO. Preferred sheet silicates are montmorillonites and bentonites; the preferred zeolite is MCM-41.

Particularly preferred support materials are spherical silica gels and aluminosilicate gels of the formula $SiO_2 \cdot a\, Al_2O_3$, where a is generally from 0 to 2, preferably from 0 to 0.5. Such silica gels are commercially available, e.g. Silica Gel SG 332, Sylopol® 948 or 952 or S 2101 from W. R. Grace or ES 70X from Crosfield.

As regards the particle size of the support material, mean particle diameters which have been found to be useful are from 1 to 300 $\mu$m, preferably from 20 to 80 $\mu$m, determined by known methods such as sieve methods. The pore volume of these supports is from 1.0 to 3.0 ml/g, preferably from 1.6 to 2.2 ml/g and particularly preferably from 1.7 to 1.9 ml/g. The BET surface area is from 200 to 750 $m^2$/g, preferably from 250 to 400 $m^2$/g.

To remove impurities, in particular moisture, adhering to the support material, the support materials can be baked before doping, with temperatures of from 45 to 1000° C. being suitable. Temperatures of from 100 to 750° C. are particularly useful for silica gels and other metal oxides. This baking can be carried out for from 0.5 to 24 hours, preferably from 1 to 12 hours. The pressure conditions depend on the process chosen; baking can be carried out in a fixed-bed process, a stirred vessel or else in a fluidized-bed process. Baking can in general be carried out at atmospheric pressure. However, reduced pressures of from 0.1 to 500 mbar are advantageous, a range from 1 to 100 mbar is particularly advantageous and a range from 2 to 20 mbar is very particularly advantageous. In the case of fluidized-bed processes, on the other hand, it is advisable to employ a slightly superatmospheric pressure in a range from 1.01 bar to 5 bar, preferably from 1.1 to 1.5 bar.

Chemical treatment of the support material with an alkyl compound such as an aluminum alkyl, a lithium alkyl or an aluminoxane is likewise possible.

In the case of a suspension polymerization process, use is made of suspension media in which the desired polymer is insoluble or soluble to only a slight extent, because otherwise deposits of product occur in the parts of the plant in which the product is separated off from the suspension medium and force repeated shutdowns and cleaning operations. Suitable suspension media are saturated hydrocarbons such as propane, n-butane, isobutane, n-pentane, isopentane, n-hexane, isohexane and cyclohexane, with isobutane being preferred.

Pressure and temperature conditions during the polymerization can be chosen within wide limits. A suitable pressure range has been found to be from 0.5 bar to 150 bar, preferably from 10 to 75 bar. A suitable temperature range has been found to be from 0 to 120° C., preferably from 40 to 100° C.

As monomers, mention may be made of the following olefins: ethylene, propylene, 1-butene, 1-pentene, 1-hexene, 1-octene, 1-decene and 1-undecene, with preference being given to ethylene.

Suitable comonomers are α-olefins, for example from 0.1 to 20 mol % of 1-butene, 1-pentene, 1-hexene, 4-methyl-1-pentene, 1-octene, 1-decene or 1-undecene. Further suitable comonomers are isobutene and styrene, also internal olefins such as cyclopentene, cyclohexene, norbornene and norbornadiene.

Furthermore, hydrogen has been found to be an effective chain transfer agent in polymerizations using the catalysts of the present invention, i.e. the molecular weight of the polymers obtainable by means of the catalysts of the present invention can be reduced by addition of hydrogen. If sufficient hydrogen is added, waxes are obtained. The hydrogen concentration required for this depends, inter alia, on the type of polymerization plant employed. Addition of hydrogen increases the activity of the catalysts of the present invention.

The catalysts of the present invention can also be used together with one or more other polymerization catalysts known per se. Thus, they can be used together with Ziegler-Natta catalysts, supported metallocene catalysts containing transition metals of groups 4 to 6 of the Periodic Table of the Elements, catalysts based on late transition metals (WO 96/23010), Fe or Co complexes with pyridyldiimine ligands, as are disclosed in WO 98/27124, or chromium oxide catalysts of the Phillips type.

If a plurality of catalysts is used, it is possible to mix various catalysts with one another and to meter them in together or to use cosupported complexes on a common support or else to meter various catalysts separately into the polymerization vessel at the same point or at various points.

It has also been found that the novel complexes of the formulae I a and I b, in particular those in which M=Ni, are particularly suitable for the polymerization or copolymerization of 1-olefins, preferably ethylene, in emulsion polymerization processes.

Apart from other 1-olefins as comonomers, for example propene, 1-butene, 1-hexene, 1-octene or 1-decene, the catalyst system of the present invention also enables polar comonomers to be incorporated, with from 0.1 to 50 mol % of comonomer being able to be used. Preference is given to acrylates such as acrylic acid, methyl acrylate, ethyl acrylate, 2-ethylhexyl acrylate, n-butyl acrylate or tert-butyl acrylate;

methacrylic acid, methyl methacrylate, ethyl methacrylate, n-butyl methacrylate or tert-butyl methacrylate;

vinyl carboxylates, particularly preferably vinyl acetate, unsaturated dicarboxylic acids, particularly preferably maleic acid, unsaturated dicarboxylic acid derivatives, particularly preferably maleic anhydride and alkylimides of maleic acid, e.g. N-methylmaleimide.

Furthermore, it is possible to prepare terpolymers comprising at least 2 of the abovementioned monomers together with ethylene.

The emulsion polymerization of the 1-olefins using the novel metal complexes of the formula I can be carried out in a manner known per se.

The order of addition of the reagents in the emulsion polymerization is not critical. Thus, the solvent can firstly be pressurized with gaseous monomer or liquid monomer can be metered in, after which the catalyst system is added. However, the solution of the catalyst system can also firstly be diluted with further solvent, after which monomer is added.

The actual polymerization usually proceeds at a minimum pressure of 1 bar; below this pressure, the polymerization rate is too low. Preference is given to 2 bar and particular preference is given to a minimum pressure of 10 bar.

The maximum practical pressure is 4000 bar; at higher pressures, the demands made on the material of construction of the polymerization reactor are very high and the process becomes uneconomical. Preference is given to 100 bar and particular preference is given to 50 bar.

The polymerization temperature can be varied within a wide range. The minimum practical temperature is 10° C., since the polymerization rate decreases at low temperatures. Preference is given to a minimum temperature of 40° C., particularly preferably 65° C. The temperature should not exceed 350° C. and is preferably not above 150° C., particularly preferably not above 100° C.

Prior to the polymerization, the complex of the formulae I a to d is dissolved in an organic solvent or in water. The solution is stirred or shaken for a number of minutes to ensure that it is clear. The stirring time can be, depending on the solubility of the compound concerned, from 1 to 100 minutes.

At the same time, any activator necessary is dissolved in a second portion of the same solvent or else in acetone.

Suitable organic solvents are aromatic solvents such as benzene, toluene, ethylbenzene, ortho-xylene, meta-xylene and para-xylene and also mixtures thereof. Further suitable solvents are cyclic ethers such as tetrahydrofuran and dioxane or acyclic ethers such as diethyl ether, di-n-butyl ether, diisopropyl ether or 1,2-dimethoxyethane. Ketones such as acetone, methyl ethyl ketone or diisobutyl ketone are also suitable, and the same applies to amides such as dimethylformamide or dimethylacetamide. It is also possible to use mixtures of these solvents with one another and mixtures of these solvents with water or alcohols such as methanol or ethanol.

Preference is given to acetone and water and mixtures of acetone and water in any mixing ratio. The amount of solvent is likewise not critical, but it has to be ensured that the complex and the activator can dissolve completely, otherwise a decrease in the activity has to be expected. The dissolution process can, if desired, be accelerated by ultrasonic treatment.

Any emulsifier which is optionally added can be dissolved in a third portion of the solvent or else together with the complex.

The amount of emulsifier is selected so that the mass ratio of monomer to emulsifier is greater than 1, preferably greater than 10 and particularly preferably greater than 20. The less emulsifier used, the better. The activity in the polymerization is significantly increased if an emulsifier is added. This emulsifier can be nonionic or ionic in nature.

Nonionic emulsifiers which can be used are, for example, ethoxylated monoalkylphenols, dialkylphenols and trialkylphenols (EO content: 3-50, alkyl radical: $C_{4}$–$C_{12}$) and ethoxylated fatty alcohols (EO content: 3-80; alkyl radical: $C_{8}$–$C_{36}$). Examples are the Lutensol® grades from BASF AG or the Triton® grades from Union Carbide.

Customary anionic emulsifiers are, for example, alkali metal and ammonium salts of alkyl sulfates (alkyl radical: $C_{8}$–$C_{12}$), of sulfuric monoesters of ethoxylated alkanols (EO content: 4-30, alkyl radical: $C_{12}$–$C_{18}$) and ethoxylated alkylphenols (EO content: 3-50, alkyl radical: $C_{4}$–$C_{12}$), of alkylsulfonic acids (alkyl radical: $C_{12}$–$C_{18}$) and of alkylarylsulfonic acid (alkyl radical: $C_{9}$–$C_{18}$).

Suitable cationic emulsifiers are generally primary, secondary, tertiary or quaternary ammonium salts, alkanolammonium salts, pyridinium salts, imidazolinium salts, oxazolinium salts, morpholinium salts, thiazolinium salts and also salts of amine oxides, quinolinium salts, isoquinolinium salts, tropylium salts, sulfonium salts and phosphonium salts, in each case containing a $C_{6}$–$C_{18}$-alkyl, -aralkyl or heterocyclic radical. Examples which may be mentioned are dodecylammonium acetate or the corresponding hydrochloride, the chlorides or acetates of the various 2-(N,N,N-trimethylammonium)ethyl esters of paraffinic acids, N-cetylpyridinium chloride, N-laurylpyridinium sulfate and also N-cetyl-N,N,N-trimethylammonium bromide, N-dodecyl-N,N,N-trimethylammonium bromide, N,N-distearyl-N,N-dimethylammonium chloride and also the gemini surfactant N,N'-(lauryldimethyl)ethylenediamine dibromide. Numerous further examples may be found in H. Stache, Tensid-Taschenbuch, Carl-Hanser-verlag, Munich, Vienna, 1981 and in McCutcheon's, Emulsifiers & Detergents, MC Publishing Company, Glen Rock, 1989.

The components, namely complex in solution, optionally the solution of the emulsifier and optionally the solution of the activator, are subsequently introduced into the polymerization reactor. Polymerization reactors which have been found to be useful are stirred vessels and autoclaves and also tube reactors, with the tube reactors being able to be configured as loop reactors.

The monomer or monomers to be polymerized is/are mixed with the polymerization medium. As polymerization medium, it is possible to use water or mixtures of water with the above-mentioned solvents. It should be ensured that the proportion of water is at least 50% by volume, based on the total mixture, preferably at least 90% by volume and particularly preferably at least 95% by volume.

The solutions of the complex, if used the activator and if used the emulsifier are combined with the mixture of monomer and aqueous polymerization medium. The order of addition of the various components is not critical per se. However, it is necessary for the components to be combined sufficiently quickly for no crystallization of any sparingly soluble complexes formed as intermediates to occur.

The process of the present invention gives polyolefins and olefin copolymers in high yields, i.e. the activity of the complexes of the present invention under the conditions of emulsion polymerization is very high.

As polymerization process, continuous and batchwise processes are suitable in principle. Preference is given to semicontinuous processes (semibatch processes) in which all components are mixed and then further monomer or monomer mixture is metered in during the polymerization.

The process of the present invention firstly gives aqueous polymer dispersions.

The mean particle diameter of the polymer particles in the dispersions obtained according to the present invention is from 10 to 1000 nm, preferably from 50 to 500 nm and particularly preferably from 70 to 350 nm. The distribution of the particle diameters can be very uniform, but does not have to be. For some applications, in particular for those in which high solids contents (>55%) are present, broad or bimodal distributions are even preferred.

The polymers obtained by the process of the present invention have industrially interesting properties. In the case of polyethylene, they have a high degree of crystallinity, which can be shown by, for example, the number of branches. Less than 100 branches, preferably less than 50 branches, per 1000 carbon atoms of the polymer, determined by $^1$H-NMR and $^{13}$C-NMR spectroscopy, are found.

The enthalpies of fusion of the polyethylenes obtainable by the process of the present invention are greater than 100 J/g, preferably greater than 140 and particularly preferably greater than 180 J/g, measured by DSC.

The molecular weight distributions of the polyethylenes obtainable by the process of the present invention are narrow, i.e. the Q values are in the range from 1.1 to 3.5, preferably from 1.5 to 3.1.

Advantages of the dispersions obtained according to the present invention are firstly their low price owing to the cheap monomers and process and, secondly, that they are more stable to weathering than are dispersions of polybutadiene or butadiene copolymers. Compared to dispersions of polymers comprising acrylates or methacrylates as main monomer, the lower tendency to undergo saponification is advantageous. A further advantage is that most olefins are volatile and unpolymerized residual monomers can easily be removed. A final advantage is that no molar mass regulators such as tert-dodecyl mercaptan which are, firstly, difficult to separate off and, secondly, have an unpleasant odor have to be added during the polymerization.

The polymer particles can be obtained as such by removal of the water and, if necessary, the organic solvent or solvents from the aqueous dispersions obtained initially. Numerous customary methods are available for removal of the water and, if necessary, the organic solvent or solvents, for example filtration, spray drying or evaporation. The polymers obtained in this way have a good morphology and a high bulk density.

The particle sizes can be determined by light scattering methods. A review may be found in D. Distler "Wäßrige Polymerdispersionen", Wiley-VCH Verlag, 1st edition, 1999, Chapter 4.

The dispersions obtained according to the present invention can be used advantageously in numerous applications, for example paper applications such as paper coating or surface sizing, also paints and varnishes, building chemicals, adhesives raw materials, molded foams, textile and leather applications, coatings on the reverse side of carpets, mattresses or pharmaceutical applications.

The following example illustrates the invention.

General Preliminary Remarks:

All work was carried out in the absence of air and moisture using standard Schlenk techniques. Apparatus and chemicals were prepared accordingly. The polymer viscosity was determin d in accordance with ISO 1628-3. The molar masses were determined by means of GPC. For the GPC measurements, the following conditions based on DIN 55672 were selected: solvent: 1,2,4-trichlorobenzene, flow: 1 ml/min, temperature: 140° C., calibration: PE standards, instrument: Waters 150C. The number of methyl groups was determined by IR spectroscopy.

Synthesis of the Imine III.1:

The starting materials, viz. 4.97 g of acetophenone

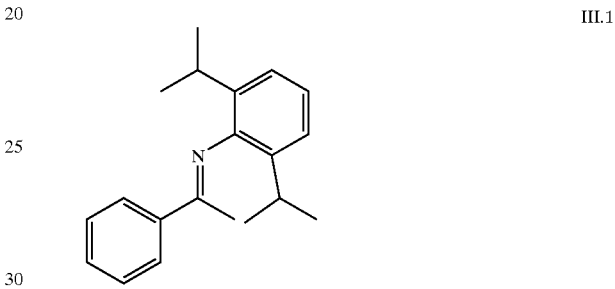

III.1

(41.4 mmol) and 7.33 g of 2,6-diisopropylaniline (41.4 mmol), were placed in a 250 ml round-bottomed flask fitted with a water separator, dissolved in 70 ml of toluene and, after addition of 500 mg of p-toluenesulfonic acid, refluxed for 2 hours. The orange solution was washed twice with H$_2$O and then once with 10% strength NaHCO$_3$ solution until neutral. The organic phase was dried over Na$_2$SO$_4$. After the solvent had been taken off on a rotary evaporator, traces of toluene and also unreacted amine and ketone were taken off in a high vacuum at 105–115° C. The oily imine crystallized overnight.

This method was used to prepare: imine III.1

Yield: 84.6%, empirical formula: C$_{20}$H$_{25}$N, color: yellow, m.p.: 68–69° C.

1H NMR (CDCl$_3$): 1.21 (12H, m, 4×CH$_3$), 2.16 (3H, s, CH$_3$), 2.83 (2H, sept., CH), 7.11–8.12 (8H, m, phenyl)

13C NMR (CDCl$_3$): 18.0, 22.9, 23.2, 28.2, 122.9, 123.3, 127.1, 128.4, 130.3, 136.0, 139.1, 146.7, 164.7 (C=N)

IR (KBr, cm$^{-1}$): 3056 (w), 2958 (m), 2867 (m), 1630 (s), 1578 (s), 1449 (s), 1366 (m), 1289 (s), 1243 (m), 1192 (m), 1111 (w), 1044 (w), 1027 (m), 969 (w), 938 (m), 822 (m), 774 (vs), 760 (vs), 735 (s), 693 (vs)

M$^+$=279.2 m/e

Synthesis of the Ligand II.1

0.18 ml of diisopropylamine (1.3 mmol) was placed in a baked-out Schlenk tube which had been flushed with argon, dissolved in 10 ml of THF (absolute) and admixed at −80° C. with n-BuLi (0.72 ml, 1.1 equivalents, 2.0 M solution in pentane). After removal of the cold bath (EtOH, N$_2$), the resulting LDA solution was stirred for ½ h at room temperature.

The imine III.1 (0.36 g, 1.30 mmol) was added to the freshly prepared LDA solution at −80° C. After removal of the cold bath, the dissolved starting material was stirred at room temperature for 2 hours and thereby deprotonated (color change: yellowish to yellow-green).

0.24 g of benzophenone (1.3 mmol) were subsequently added at room temperature and the mixture was stirred overnight.

The yellow THF solution was then poured into 100 ml of ice water and extracted three times with 25 ml each time of diethyl ether. The combined organic phases were washed with $H_2O$, dried over $Na_2SO_4$ and the organic solvents were removed on a rotary evaporator. The yellow product crystallized over a period of 2 hours. Subsequent recrystallization from ethyl acetate/hexane gave the pure β-hydroxyimine II.1.

Ligand II.1

Yield: 72%, empirical formula: $C_{33}H_{35}NO$, color: whitish yellow, m.p.: 121–122° C.

1H NMR ($CDCl_3$): 0.61 (6H, d, 2×$CH_3$), 0.82 (6H, d, 2×$CH_3$), 2.19 (2H, sept, CH), 3.76 (2H, s, $CH_2$), 6.80–7.51 (19H, m, phenyl, OH)

II.1

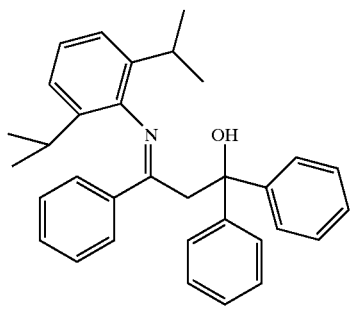

13C NMR ($CDCl_3$): 22.0, 24.5, 27.9 ($CH_3$, CH), 48.4 ($CH_2$), 78.5 (C—OH), 122.9, 124.2, 126.0, 126.7, 127.0, 128.1, 128.2, 128.3, 129.5, 130.0, 132.4, 136.8, 137.6, 143.6, 147.4 (phenyl), 170.4 (C=N)

IR (KBr, cm$^{-1}$): 3288 (m, broad), 3062 (w), 2962 (m), 2925 (w), 2867 (m), 1634 (vs), 1492 (m), 1453 (vs), 1343 (m), 1227 (m), 1065 (m), 1042 (s), 1015 (s), 942 (s), 917 (m), 899 (s), 805 (m), 749 (vs), 700 (vs), 637 (s) M$^+$=461.3 m/e Polymerization:

46 mg (0.1 mmol) of ligand II.1 and 40 mg (0.22 mmol) of $(CH_3)_2Ni(TMEDA)$ were added to 250 ml of toluene in a 1 l steel autoclave and were mixed by stirring. The autoclave was subsequently pressurized with 40 bar of ethylene and polymerization was carried out at 70° C. for 120 minutes. This gave 3.3 g of polyethylene, which corresponds to an activity of 7.5 kg of polyethylene/mol of Ni.h.

TMEDA: Tetramethylethylenediamine.

We claim:

1. A complex having one of the formulae I a to d,

Ia

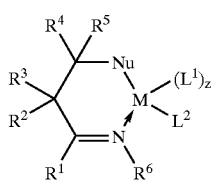

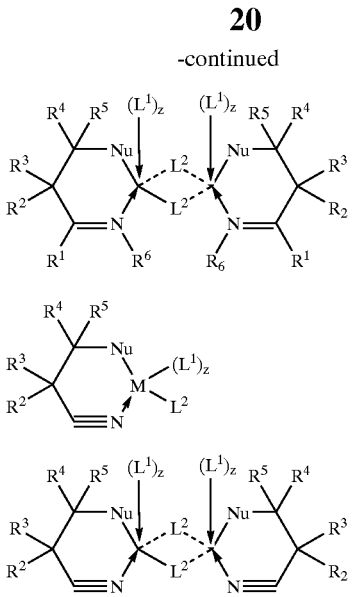

where the variables are defined as follows:

M is an element of groups 6 to 10 of the Periodic Table of the Elements in the oxidation state +2 to +4;

Nu is selected from the group consisting of O, S and N—R$^7$;

R$^1$ to R$^7$ to are selected from among hydrogen, $C_1$–$C_{18}$-alkyl, substituted or unsubstituted, $C_2$–$C_{18}$-alkenyl, substituted or unsubstituted, having from one to 4 isolated or conjugated double bonds;

$C_3$–$C_{12}$-cycloalkyl, substituted or unsubstituted, $C_7$–$C_{13}$-aralkyl, $C_6$–$C_{14}$-aryl, unsubstituted or substituted by one or more identical or different substituents selected from the group consisting of $C_1$–$C_8$-alkyl, substituted or unsubstituted, $C_3$–$C_{12}$-cycloalkyl, $C_7$–$C_{13}$-aralkyl, $C_6$–$C_{14}$-aryl, halogen, $C_1$–$C_6$-alkoxy, substituted or unsubstituted, $C_6$–$C_{14}$-aryloxy, SiR$^8$R$^9$R$^{10}$ and O—SiR$^8$R$^9$R$^{10}$;

five- and six-membered nitrogen-containing heteroaryl radicals, unsubstituted or substituted by one or more identical or different substituents selected from the group consisting of $C_1$–$C_8$-alkyl, substituted or unsubstituted, $C_3$–$C_{12}$-cycloalkyl, $C_7$–$C_{13}$-aralkyl, $C_6$–$C_{14}$-aryl, halogen, $C_1$–$C_6$-alkoxy, $C_6$–$C_{14}$-aryloxy, SiR$^8$R$^9$R$^{10}$ and O—SiR$^8$R$^9$R$^{10}$;

where adjacent radicals $R^1$ to $R^7$ may be joined to one another to form a 5- to 12-membered non-aromatic ring;

$L^1$ is an uncharged, organic or inorganic ligand, $L^2$ is an organic or inorganic anionic ligand, where $L^1$ and $L^2$ may be joined to one another by one or more covalent bonds, z is an integer from 1 to 3, $R^8$ to $R^{10}$ are identical or different and are selected from the group consisting of hydrogen, $C_1$–$C_8$-alkyl, $C_3$–$C_{12}$-cycloalkyl, $C_7$–$C_{13}$-aralkyl and $C_6$–$C_{14}$-aryl.

2. The complex as claimed in claim 1, wherein M is selected from the group consisting of nickel and palladium.

3. The complex as claimed in claim 1, wherein
$L^1$ is selected from the group consisting of
phosphines $(R^{11})_x PH_{3-x}$,
amines $(R^{11})_x NH_{3-x}$,
ethers $(R^{11})_2 O$,
$H_2O$,
alcohols $(R^{11})OH$,
pyridine,
pyridine derivatives of the formula $C_5H_{5-x}(R^{11})_x N$,
CO,
$C_1$–$C_{12}$-alkylnitriles,
$C_6$–$C_{14}$-arylnitriles and
ethylenically unsaturated double bond systems,
where x is an integer from 0 to 3;
$L^2$ is selected from the group consisting of
halide ions,
amide ions $(R^{11})_{x-1}NH_{2-x}$,
$C_1$–$C_6$-alkyl anions,
allyl anions,
benzyl anions and aryl anions;
the radicals $R^{11}$ are identical or different and are selected from the group consisting of hydrogen, $C_1$–$C_8$-alkyl, $C_3$–$C_{12}$-cycloalkyl, $C_7$–$C_{13}$-aralkyl and $C_6$–$C_{14}$-aryl.

4. A process for preparing the complex as claimed in claim 1, which comprises firstly deprotonating a ligand of the formula II a or II b

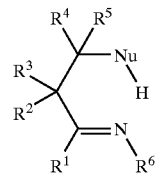

II a

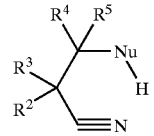

II b with a base and subsequently reacting the product with from 0.2 to 5 equivalents of a metal compound $MX_4$, $MX_3$, $ML^1L^2$ or $MX_2$, where X is halogen, $C_1$–$C_8$-alkyl, $C_3$–$C_{12}$-cycloalkyl, $C_7$–$C_{13}$-arallcyl or $C_6$–$C_{14}$-aryl and where $MX_2$, $MX_3$ or $MX_4$ may optionally be stabilized by further uncharged ligands.

5. A process for the polymerization or copolymerzation of olefins comprising polymerizing one or more olefin monomers in the presence of the complex of claim 1.

6. A process for preparing a supported catalyst for the polymerization or copolymerization of olefins, which comprises depositing one or more complexes as claimed in claim 1, and optionally an activator, on a solid support.

7. A supported catalyst for the polymerization or copolymerization of olefins which is prepared as set forth in claim 6.

8. A process for the polymerization or copolymerization of olefins comprising polymerizing one or more olefin monomers in the presence of the supported catalyst as claimed in claim 7.

9. A process for the emulsion polymerization or copolymerization of ethylene or other 1-olefins and optionally further olefins comprising polymerizing ethylene or other 1-olefins and optionally further olefins in the presence of the complex as claimed in claim 1.

* * * * *